(12) United States Patent
Jasper

(10) Patent No.: US 8,721,326 B2
(45) Date of Patent: May 13, 2014

(54) ORTHODONTIC APPLIANCE FOR BITE CORRECTION

(71) Applicant: James J Jasper, Fairview, OR (US)

(72) Inventor: James J Jasper, Fairview, OR (US)

( * ) Notice: Subject to any disclaimer, the term of this patent is extended or adjusted under 35 U.S.C. 154(b) by 0 days.

(21) Appl. No.: 13/875,932

(22) Filed: May 2, 2013

(65) Prior Publication Data

US 2013/0236849 A1    Sep. 12, 2013

Related U.S. Application Data

(63) Continuation-in-part of application No. 13/290,292, filed on Nov. 7, 2011, now Pat. No. 8,529,253.

(51) Int. Cl.
     *A61C 3/00*      (2006.01)

(52) U.S. Cl.
     USPC .............................................. 433/19

(58) Field of Classification Search
     USPC ................. 433/18–19, 21–22, 5, 7, 179
     See application file for complete search history.

(56) References Cited

U.S. PATENT DOCUMENTS

| 2,876,540 | A  | * | 3/1959 | Heydenreich | 433/179 |
| 2008/0138759 | A1 | * | 6/2008 | Kravitz et al. | 433/21 |
| 2012/0058444 | A1 | * | 3/2012 | Allesee | 433/21 |

* cited by examiner

*Primary Examiner* — Heidi M Eide

(74) *Attorney, Agent, or Firm* — Mark S. Hubert

(57) ABSTRACT

A bite-correcting orthodontic appliance attaches directly to the elements of braces (i.e., brackets and archwires); flexes in its distal 25-45% to stay away from the food bolus; has a reduced elliptical profile for patient comfort; and introduces gentle force vectors to the patient's upper and lower teeth that sweep in an arch to lift up on the front of the molar and down on the lower front teeth as the appliance tries to return to its preinstalled (passive) state, resulting in rapid, yet gentle changes unseen in the orthodontic industry. Various attachment members are disclosed allowing for ease of installment in the patient's mouth.

5 Claims, 12 Drawing Sheets

FIG. 3
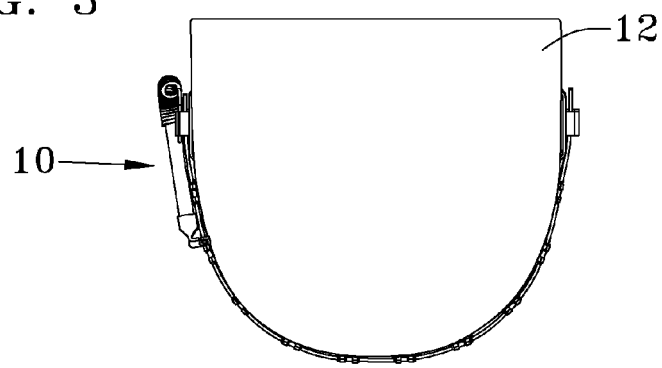
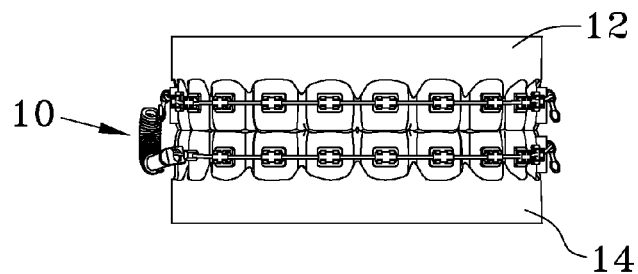
FIG. 4
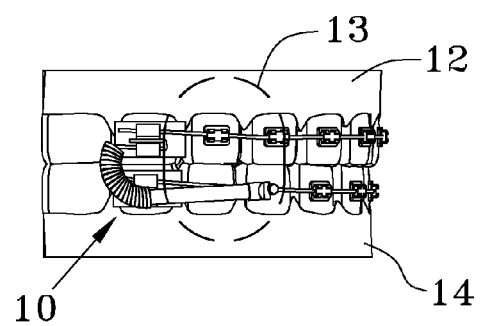
FIG. 5
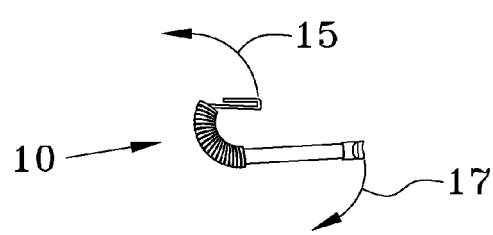
FIG. 6

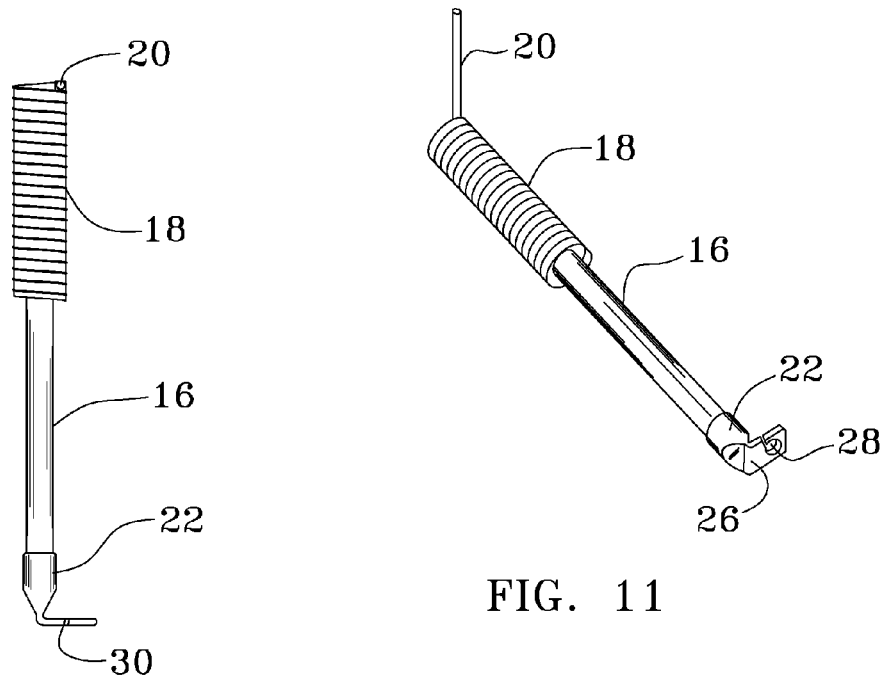
FIG. 10
FIG. 11
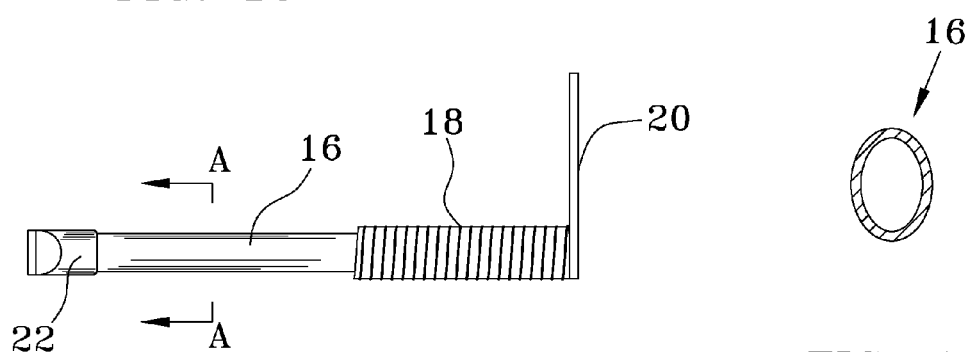
FIG. 12
FIG. 13

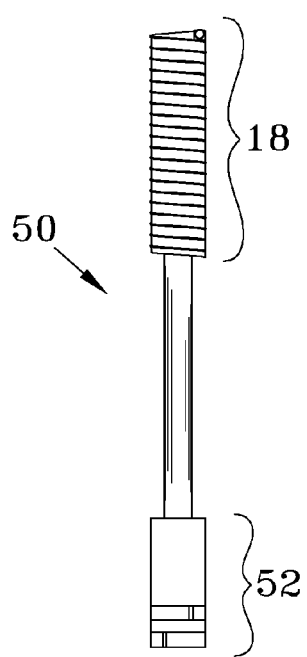
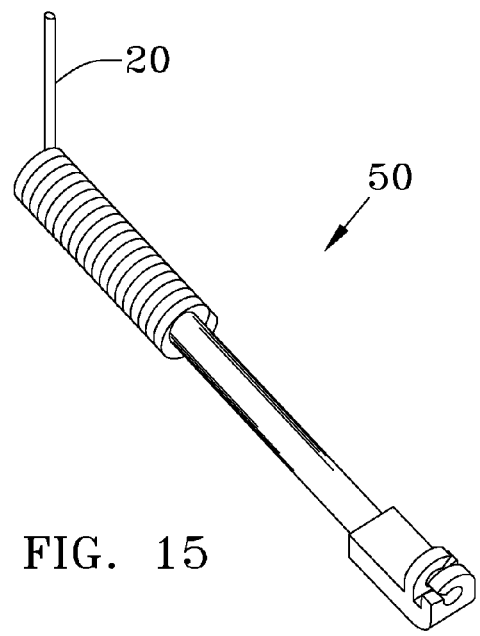
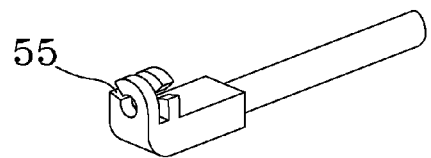
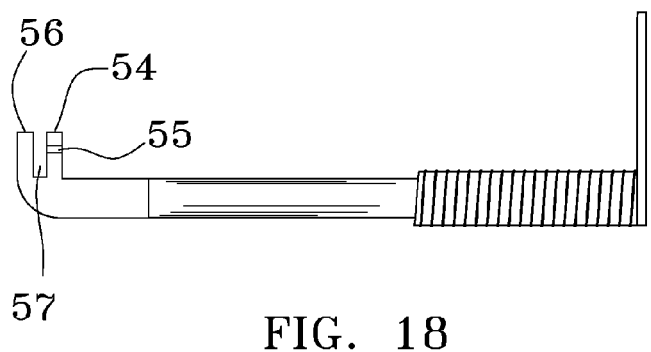
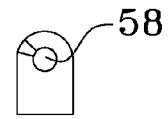
FIG. 16
FIG. 15
FIG. 17
FIG. 18
FIG. 19

FIG. 25
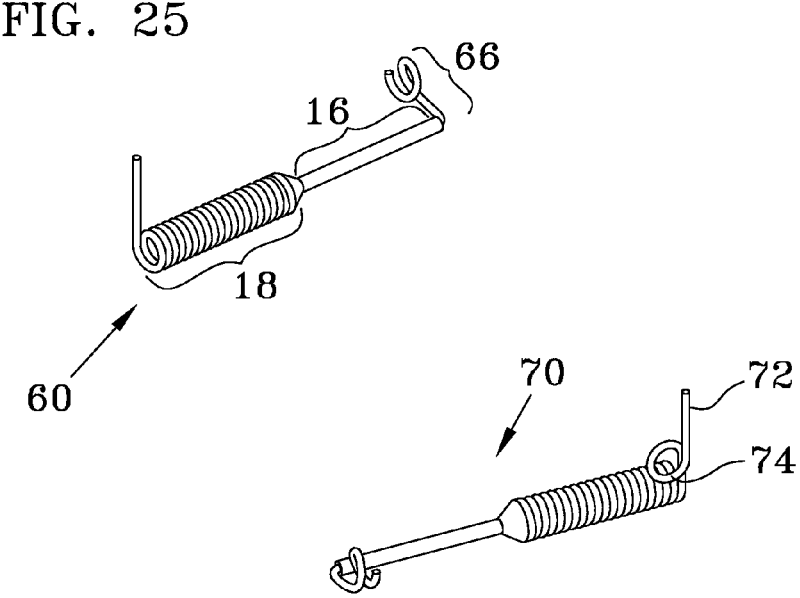
FIG. 26
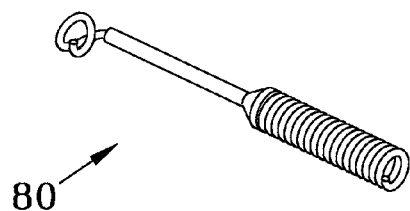
FIG. 27
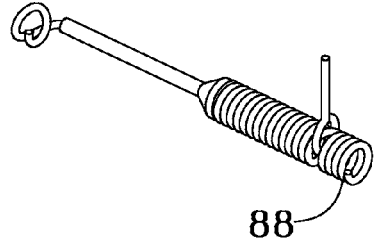
FIG. 28

ORTHODONTIC APPLIANCE FOR BITE CORRECTION

CLAIM FOR DOMESTIC PRIORITY

This application is a Continuation In Part of pending U.S. patent application Ser. No. 13/290,292 filed Nov. 7, 2011 and under 35 U.S.C. §120 claims the benefit thereof.

BACKGROUND OF THE INVENTION

The incorrect positioning of teeth or the misalignment of teeth between the upper dental arch and lower dental arch are known as malocclusions. Malocclusions are categorized by dental health professionals in three classifications: Class I—the jaw relationship is normal but individual teeth (whether located on the upper or lower dental arch) have problems such as spacing, crowding, etc., and do not achieve a good fit with the corresponding teeth on the opposite arch. Class II—commonly referred to as an overbite, the upper jaw is not in proper position, and an increased projection of the upper teeth in front of the lower teeth results. This lack of contact between the front teeth allows them to keep erupting or extruding, from the gum line into the mouth until they contact something, usually the palate. This over-extrusion, especially of the lower front teeth, requires the orthodontist to place intrusive forces on these teeth during treatment. Finally, Class III—wherein the upper dental arch rests behind the lower dental arch when the mouth is closed, commonly referred to as an underbite.

The orthodontic treatment of the aforementioned malocclusions often employs the use of the ubiquitous braces. Unfortunately, braces (that is the combination of brackets, placed on individual teeth, and an archwire connecting each bracket to guide the movement of teeth) do not correct the relationship of the upper and lower dental arches (Class II and Class III malocclusions). Additional orthodontic appliances, that provide either a pulling or pushing force must be used in order to restrict or encourage (by pulling or pushing) the jaw into its proper bite position, actually forcing the jawbones and muscles to physically adapt or "learn" the correct bite positioning.

Several bite-correcting appliances are used, often concurrently (if possible) with braces to limit the length of time of orthodontic treatment. Discussed in detail in U.S. Pat. No. 4,708,646, incorporated by reference herein, bite-correcting appliances include patient-removable appliances such as rubber bands, headgear, and molded mouthpieces. The downfall of all patient-removable appliances is that they are removable by the patient. The patient simply forgets to replace the appliance after eating, for example, thereby creating unpredictably in both the length of time of treatment, and even the treatment results, since a non-compliant patient can undo the gains of earlier treatment or produce no results.

Non-removable bite-correcting appliances are also employed. One of the most common is the "Herbst" device, developed in the early 1900's by Dr. Herbst. The Herbst device and Herbst-like devices are comprised of a rigid bar, in which each end of the bar is affixed to the lower and upper dental arches, forcing the lower dental arch forward into the desired occlusion position. The bar exerts excessive forces at its attachment points, transmitting the entire biting force of the teeth (100 pounds) to the attachment points. As a result, stainless steel crowns have to be cemented to the anchoring (attachment) teeth; the brackets of braces simply cannot handle the force. In addition to being difficult to install and generating excessive forces, another drawback, to the Herbst and Herbst-like devices is that their rigidity and placement makes both the chewing of food and hygiene incredibly difficult for the patient, as the devices cross through the area where the food is chewed.

The device disclosed in U.S. Pat. No. 4,708,646, often referred to as the "Jasper Jumper" alleviated many of the Herbst shortcomings. The rigid bar was replaced by a coiled spring, encased in a rubber sheath with attachment flanges at each end. One attachment flange would be secured to the bracket located on an upper molar tube of the patient's braces, while the second flange was secured on the archwire of the patient's braces located on the lower jaw. The Jumper generated a flexible pushing force, light enough (4-8 ounces) to be connected to braces, and generating a corrective force along the normal growth line of the face, allowing minimal discomfort for the patient. The flex-point of the spring was located in the middle of the spring, allowing the patient to better chew food and clean his/her teeth. The Jumper design, however, was prone to failure, simply breaking in the patient's mouth.

Additionally, the Jumper, the Herbst, and the Herbst clones all cross directly through the food chewing zone, when people eat. The food bolus (ball) is processed on the front side of the first molars and the second premolars as a half-inch ball. All of the aforementioned appliances, whether rigid or flexible, cross directly in the path of the food bolus making chewing and brushing cumbersome and uncomfortable.

To date, the bite-correcting appliances have been inadequate from both the physician's and patient's view, requiring improvement in durability, ease of installation/replacement, wearability, and first and foremost, function; by removing the extrusive force vectors that the prior art appliances place on the jaws/teeth; so as to obtain the desired bite correction in a short timeframe.

SUMMARY OF THE INVENTION

At the heart of the present invention is the discovery as to why the Jumper, the Herbst, and the Herbst clones were prone to failure. The Jumper's combination of the rubber coating and its ability to flex at its midpoint allowed the patient to chew on the device, typically resulting in breakage. The Jumper would push upward on distal side of the upper molars, making the roots of the molars tip forward, in a clockwise rotation, towards the front (opening) of the mouth. While the roots of the molars tip forward, the crown of the molar tips back, because the molars are connected to the front teeth via the archwire, tipping the back of the molars up, places extrusive (downward) pressure on the upper incisors (front teeth). As disclosed in the background, the front teeth of a Class II patient are already over erupted, so it is always contraindicated to place extrusive vectors on the front teeth. The Herbst and its clones also function in this way—pushing upward on the distal side of the upper molars resulting in the crown of the molars tipping back. The Jumper, the Herbst, and the Herbst clones, all deliver their forces straight along the axis of the appliance, and since they all attach to the distal of the upper molars, often with what amounts to be a small lever arm (i.e. the connection mechanism between the appliance and molar), the tipping force was magnified.

In accordance with the invention then, a bite-correcting orthodontic appliance is provided that attaches directly to the elements of braces (i.e., brackets and archwires); flexes in its distal 25-45% of the overall appliance length, to stay away from the food bolus; has a reduced profile for patient comfort; introduces unique attachment member for both easy install on the practitioner side and ease of uninstall on the patient side (should a breakage occur); and introduces gentle intrusive force vectors to the patient's upper and lower teeth that are not along the appliance's axis but instead sweep in an arch to lift up on the front of the upper molar and down on the lower front teeth as the appliance tries to return to its preinstalled (passive) state, resulting in rapid, yet gentle changes unseen in the orthodontic industry, unexpectedly reducing treatment times significantly.

BRIEF DESCRIPTION OF THE DRAWINGS

FIG. 3 a top view of the orthodontic appliance of the present invention installed on a dental model, with the dental model in a closed position;

FIG. 4 is a front view of the orthodontic appliance of the present invention installed on a dental model, with the dental model in a closed position;

FIG. 5 is a left-side view of the orthodontic appliance of the present invention installed on a dental model, with the dental model in a closed position; also illustrated is the food bolus region, indicated with a dashed line;

FIG. 6 is a left-side view of the orthodontic appliance of the present invention in its flexed state; the curved rays illustrate the path required for the appliance to return to its passive (unflexed) state;

FIG. 10 is a top view of the orthodontic appliance of the present invention;

FIG. 11 is a left-side perspective view of the orthodontic appliance of the present invention;

FIG. 12 is a right-side view of the orthodontic appliance of the present invention; and FIG. 13 is an enlarged cross-section taken along line A-A show on FIG. 12.

FIG. 15 is a left-side perspective view of a second alternate embodiment orthodontic appliance of the present invention;

FIG. 16 is a top view of a second alternate embodiment orthodontic appliance of the present invention;

FIG. 17 is a partial right-side perspective view of the attachment head of a second alternate embodiment orthodontic appliance of the present invention;

FIG. 18 is a right-side view of a second alternate embodiment orthodontic appliance of the present invention;

FIG. 19 is a front view of a second alternate embodiment orthodontic appliance of the present invention;

FIG. 25 is a back left-side perspective view of a third alternate embodiment orthodontic appliance of the present invention;

FIG. 26 is a right-side perspective view of a fourth alternate embodiment orthodontic appliance of the present invention;

FIG. 27 is a back right-side perspective view of a fifth alternate embodiment orthodontic appliance of the present invention;

FIG. 28 is a back right-side perspective view of a fifth alternate embodiment orthodontic appliance of the present invention with a pin-loop installed;

DETAILED DESCRIPTION

Figure 1:
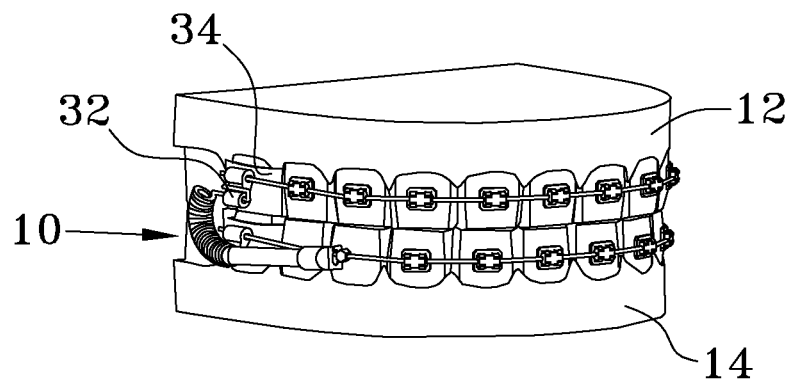
FIG. 1 is a left-side perspective view of the orthodontic appliance of the present invention installed on a dental model, with the dental model in a closed position.
Figure 2:
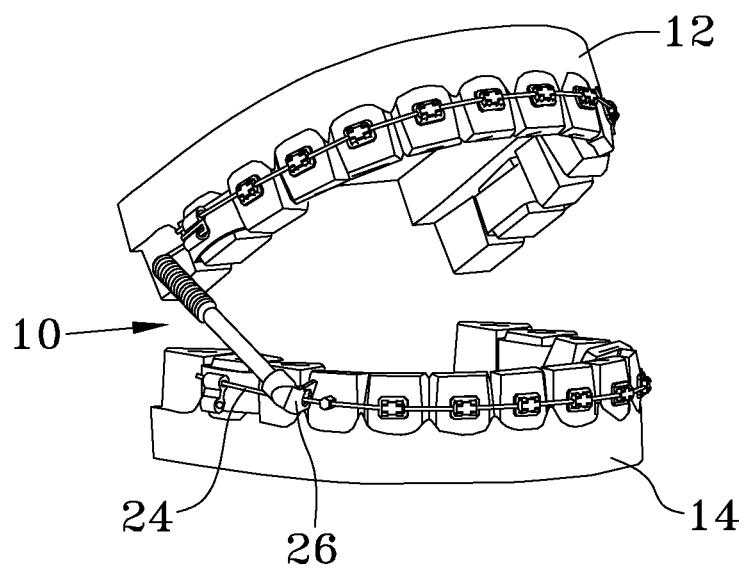
FIG. 2 is a left-side perspective view of the orthodontic appliance of the present invention installed on a dental model, with the dental model in a partially open position.
Figure 7:
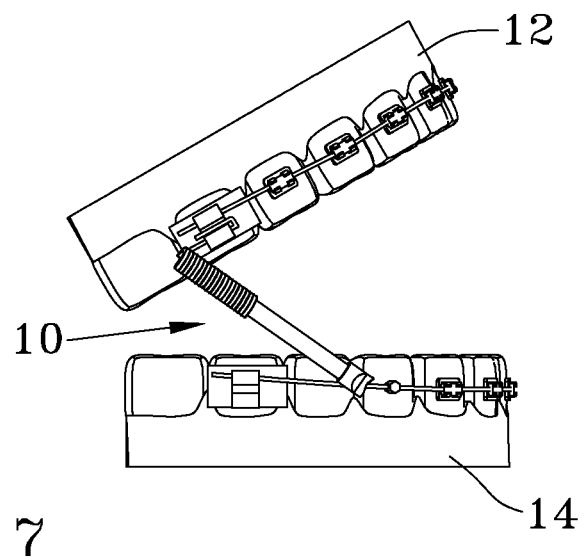
FIG. 7 is a left-side view of the orthodontic appliance of the present invention installed on a dental model, with the dental model in a partially open position.
Figure 8:
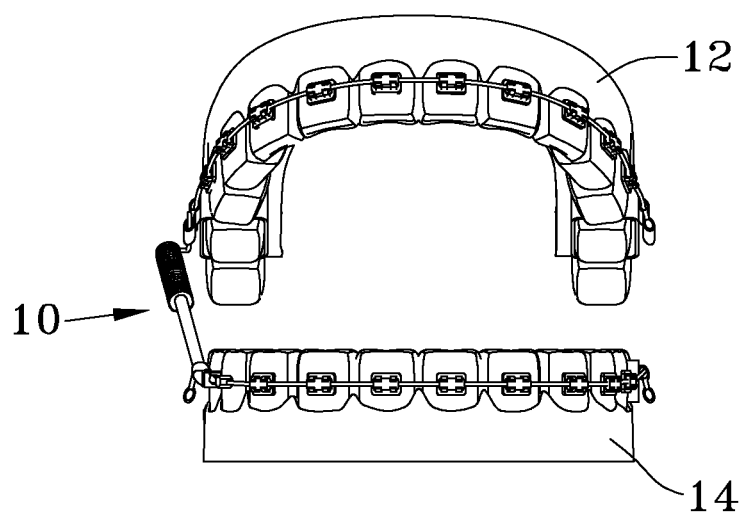
FIG. 8 is a front view of the orthodontic appliance of the present invention installed on a dental model, with the dental model in a partially open position.
Figure 9:
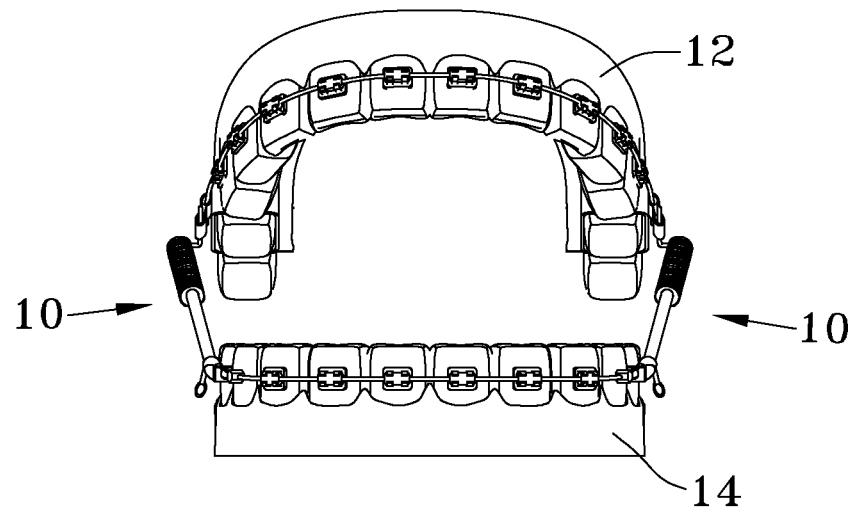
FIG. 9 is a front view of the orthodontic appliance of the present invention installed on the right-side and on the left-side of the dental model, with the dental model in a partially open position.

Referring generally to FIGS. 1-8 an orthodontic appliance 10 according to the present invention is connected to both the upper dental arch 12 (maxillary jaw) and the lower dental arch 14 (mandibular jaw). As installed in FIGS. 1-8, appliance 10 will reposition the upper dental arch 12 by placing forces on the upper molars (maxillary), causing their root tips (not illustrated) to move backwards (that is towards the back of the throat) first, putting intrusive forces on the front upper and lower incisors, and over a period of months correcting even the most severe overbites (Class II malocclusions).

Turning to FIGS. 10-12, appliance 10 is shown in its passive state and is comprised of a rigid member 16, a force generating vector control module 18, a rear attachment wire 20, and attachment member 22. Preferably, rigid member 16 is made of 3/32 (0.093 inch) stainless steel and is elliptical in shape. Shown in enlarged cross-section, the elliptical shape is clearly visible in FIG. 13. It should be noted that rigid member 16 can be made of different rigid materials including steel or plastic, and can have other cross sections including circular, square, rectangular, and flat. While illustrated as a tube (hollow) in FIG. 13, rigid member 16 could also be solid in construction.

Vector control module 18, is an elliptical or circular shaped torsion spring, preferably coiled from a rectangular, or round wire, which is an alloy of stainless steel containing Cobalt, Chromium, and Nickel, that is able to be formed in its soft state and then heat treated to create spring steel. However, any variety of metals can be used to fabricate the coil, including Nickel Titanium. Durability and the ability to deliver the forces in the range of 4 to 8 ounces are the main factors for choosing the appropriate material from which to form the vector control module 18. Specifically, and preferably, 0.025 inch stainless steel, round wire has produced the desired forces of 4 to 8 ounces under experimental conditions.

Figure 14:
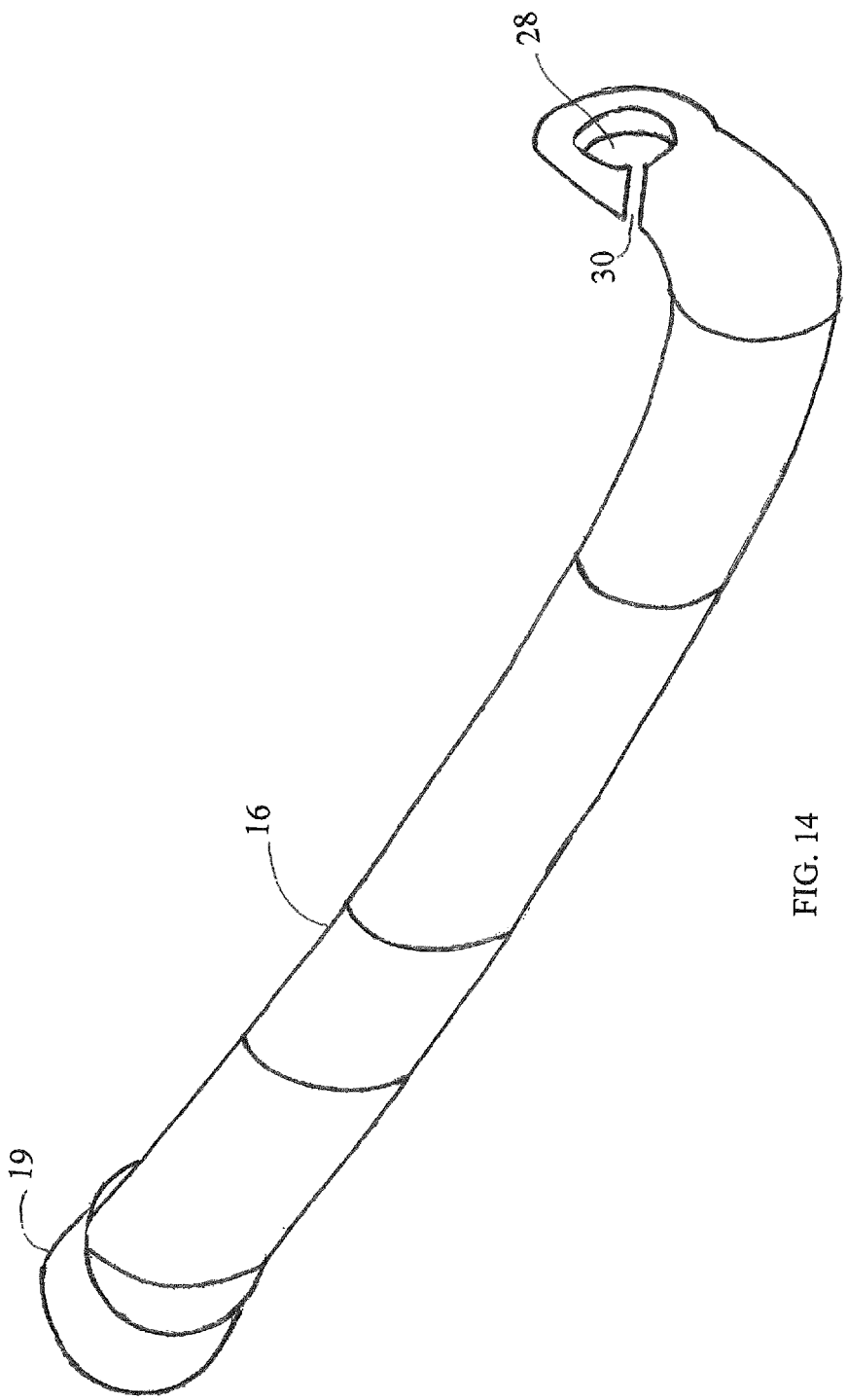
FIG. 14 is an enlarged left-side perspective view of an alternate embodiment of the rigid member and mounting link of the present invention.

The elliptical shape of both the rigid member 16 and vector control module 18 increases patient comfort, since the elliptical shape allows the minor axis of rigid member 16/vector control module 18 to reside in the horizontal plane between the patient's gum line and cheek, while providing increased strength, since the major axis resides generally perpendicular to the gum line. The elliptical shape provides the perfect combination of comfort, food flow, and strength. Variations of the structure of the rigid member 16 and vector control module 18 can accomplish the desired results provided that the end of rigid member 16 that is affixed to vector control module 18 is matingly configured to accept the end of the vector control module 18. For example, a rectangular solid linear member with an elliptical mounting-end (or circular mounting-end for a cylindrical coil) would meet the necessary structural requirements. In an alternate embodiment, illustrated as FIG. 14, a circular mounting end 19 is formed on an elliptical rigid member 16 as a connection point to a cylindrical vector control module 18. Vector control module 18 is then soldered, welded, or glued to rigid member 16, such that vector control module 18 comprises approximately 33% of the length of appliance 10. To give an idea of size, rigid member 16 is approximately 24 mm long, while the vector control module is approximately 12 mm long. These lengths are simply an approximation as appliance 10 will be made in different lengths (small, medium, and large) to accommodate different sized mouths. However, the vector control module will still comprise approximately 33% of the length of appliance 10, keeping the flex point (midpoint) of the vector control module 18 to the distal 25-45% of appliance 10.

Continuing with FIGS. 10-12, rear attachment wire 20 is an unwound extension of the wire comprising the vector control module 18. It extends normally from the linear axis of the vector control module 18. Attachment member 22 is for adjustable connection with archwire 24 located on the braces assembly of the lower dental arch 14. For quick yet secure attachment with archwire 24, attachment member 22 has a flat portion 26, which resides at an orientation of approximately 90° from the longitudinal axis of appliance 10. Portion 26 contains an orifice 28 formed therethrough and receiving slot 30 that runs from the central orifice 28 to the peripheral edge of the portion 26. Slot 30 allows the appliance to be removed or installed without removing the archwire 24 as was previously required with prior art appliances. Attachment member 22 is soldered, welded, or glued to rigid member 16, and can be made of stainless steel, or any rigid, durable material including steel or plastic. Turning again to an alternate embodiment illustrated in FIG. 14, it can be seen that circular mounting end 19, rigid member 16, and attachment member 22 are cast as a single unit (one piece).

Returning to FIGS. 1-9, it can be seen that appliance 10 is secured within a patient's mouth via standard braces. Specifically, referring to FIG. 2 it can be seen that archwire 24 is contained within orifice 28 of flat portion 26. The orthodontist simply connects appliance 10 to archwire 24 via receiving slot 30, and then bends the slot closed, allowing for quick installation and/or removal if there is breakage of appliance 10. Next, the orthodontist secures rear attachment wire 20 to the patient's upper dental arch 12 via headgear tube 32 which resides on standard molar bands 34, as is visible in FIGS. 1 & 5, by simply inserting rear attachment wire 20 through the distal end of headgear tube 32, and then bends wire 20 back towards the distal end of headgear tube 32, such that when properly secured to the upper dental arch 12, wire 20 forms a c-shaped hook through tube 32 as shown in FIG. 5.

Moving the flex point of appliance 10—that is the midpoint of the vector control module 18, to the distal 25-40% of the appliance 10's length accomplishes three things: 1) it cannot bend between the teeth to be chewed on and broken, 2) it causes rigid member 16 to reside below the food bolus area 13 (See FIG. 5) to make eating more comfortable, and 3) the intrusive force vectors generated by the installed orthodontic appliance 10 result in correction of the most severe overbites/underbites, as further described below. Prior art appliances flexing at the midpoint of the appliance, place axial vectors on the upper and lower jaws, rather than the sweeping vectors of the present invention.

An enormous improvement over prior art appliances, appliance 10 does not deliver its force straight along its axis to the distal side of the molars. Attachment wire 20 is connected directly to the vector control module 18 without a hinge, allowing appliance 10, as shown in FIG. 6, to return to its passive, pre-installed state (FIG. 11) in a sweeping motion 15, lifting up on the front (closest to the mouth opening) of the molar tube 32, while ray 17 illustrates the sweeping force placed on the mandible 14. This is best illustrated in FIG. 6. FIG. 6 shows appliance 10 in its installed shape—that is, the same shape that can be seen in FIG. 5. The rays, 15 and 17, indicate the direction appliance 10 moves in order to return to its pre-installed/passive state. While FIG. 6 is not a free body diagram, it is not hard to imagine while looking at FIG. 6 in conjunction with FIG. 5, how appliance 10 lifts up on the front of the molar tube 32 causing the roots (not illustrated) of the upper molars to tip toward the back of the mouth prior to the whole tooth moving distal. Since the molars are connected to the front teeth via the archwire 24, intrusive and backward vectors are placed on the upper incisors. The mandubular front teeth receive an equal and opposite force, shown in FIG. 6 as ray 17 illustrates pushing downwards and forward on these teeth, intruding them to compensate for their over-erupted condition at the start of treatment mentioned in the Background.

It should be understood that while this disclosure focuses on Class II malocclusions, appliance 10 is suitable for use in correcting Class III malocclusions as well. For Class III applications, appliance 10 is placed in the mouth upside down—that is rear attachment wire is connected to lower molar bands (mandibular) and attachment member 22 slides onto the upper archwire (as opposed to the lower) via receiving slot 30. Once installed, appliance 10 will push the mandible 14 backwards, and provide pushing vectors on the upper front teeth, resulting in the repositioning of the maxilla to the desired position.

FIGS. 15-19 illustrate a second embodiment orthodontic appliance 50 of the present invention, in which a twin-tab attachment member 52 is employed. Rigid member 16, force generating vector control module 18, and rear attachment wire 20, are all identical in construction and function as the previously discussed embodiment illustrated in FIGS. 10-12. Twin-tab attachment member 52 is comprised of mirror image twin-tabs 54, 56 each containing an attachment orifice 58 therethrough and an attachment slot 55 that runs from the attachment orifice 58 to the peripheral edge of each twin-tab. Attachment slots 55 allows the appliance to be removed or installed without removing the archwire 24 as was previously required with prior art appliances. Twin-tabs 54, 56 are separated by installation gap 57, best illustrated in FIG. 18.

Figure 20A:
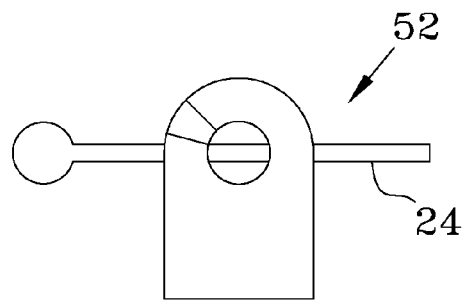
FIG. 20A illustrates the first step for installing second alternate embodiment orthodontic appliance on a section of archwire from a top view (just the attachment member is shown for visual clarity)
Figure 21A:
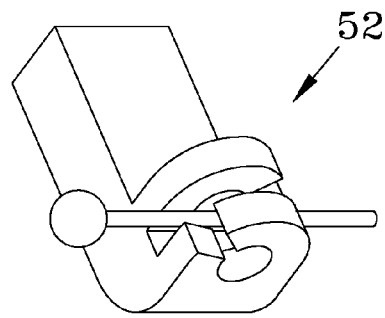
FIG. 21A illustrates the first step for installing second alternate embodiment orthodontic appliance on a section of archwire from a front perspective view (just the attachment member is shown for visual clarity)
Figure 20B:
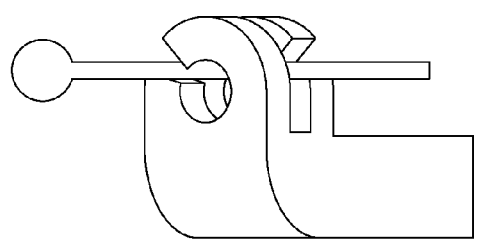
FIG. 20B illustrates the second step for installing second alternate embodiment orthodontic appliance on a section of archwire from a top view (just the attachment member is shown for visual clarity)
Figure 21B:
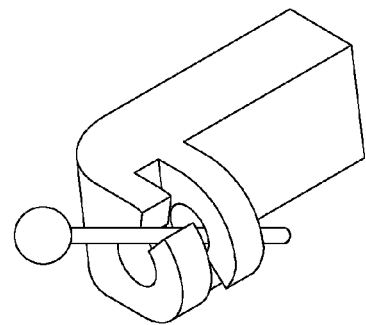
FIG. 21B illustrates the second step for installing second alternate embodiment orthodontic appliance on a section of archwire from a front perspective view (just the attachment member is shown for visual clarity)
Figure 20C:
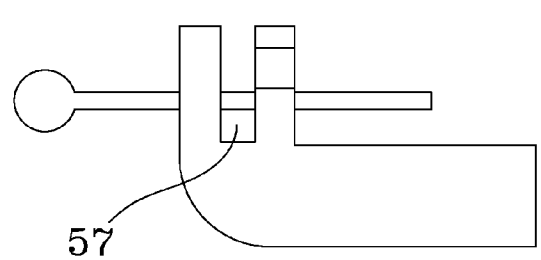
FIG. 20C illustrates the third step for installing second alternate embodiment orthodontic appliance on a section of archwire from a top view (just the attachment member is shown for visual clarity)
Figure 21C:
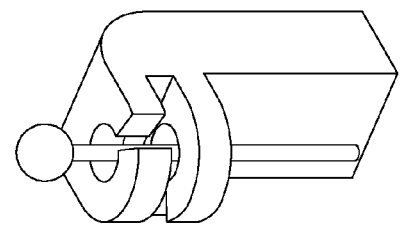
FIG. 21C illustrates the third step for installing second alternate embodiment orthodontic appliance on a section of archwire from a front perspective view (just the attachment member is shown for visual clarity)

FIGS. 20A-20C and 21A-21C illustrate how second embodiment orthodontic appliance 50 is installed on an archwire 24. For visual clarity twin-tab attachment member 52 is only illustrated. FIGS. 21A-21C simply illustrate the same installation series reflected in FIGS. 20A-20C from an inside of the mouth view. The orthodontist (or other dental practitioner) first positions the attachment member 52 (oriented vertically) around the archwire 24, such that the archwire resides between twin-tabs 54, 56 and along installation gap 57 (See FIGS. 20A and 21A). The practitioner then simply rotates attachment member 52 (appliance 50) until attachment member 52 resides parallel to archwire 24, as illustrated in FIG. 20C and FIG. 21C. FIG. 20B illustrates an approximate 45° rotation from FIG. 20A, and FIG. 20C illustrates an approximate, additional 45° rotation of attachment member from FIG. 20B. Attachment member 52 rotates approximately 90° degrees from its position in FIG. 20A (or FIG. 21A) to FIG. 20C (or FIG. 21C). FIGS. 20C and 21C illustrate attachment member 52 locked onto archwire 24. Should appliance 50 break in a patient's mouth, the twin-tab construction of attachment member 52, allow the patient to remove the appliance (breakage typically occurs on vector control module 18) from his/her mouth until he/she can see his/her orthodontist. It should be noted that while the twin-tab attachment member 52 is illustrated with a generally rectangular body, it could smoothly transition into rigid member 16, possibly even being cast as one solid piece.

Figure 22:
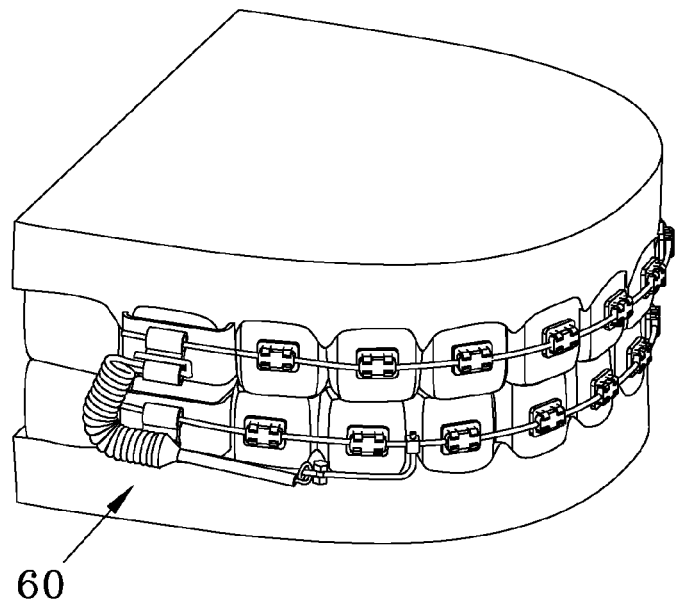
FIG. 22 is a left-side perspective view of a third alternate embodiment of the orthodontic appliance of the present invention installed on a dental model, with the dental model in a closed position.
Figure 23:
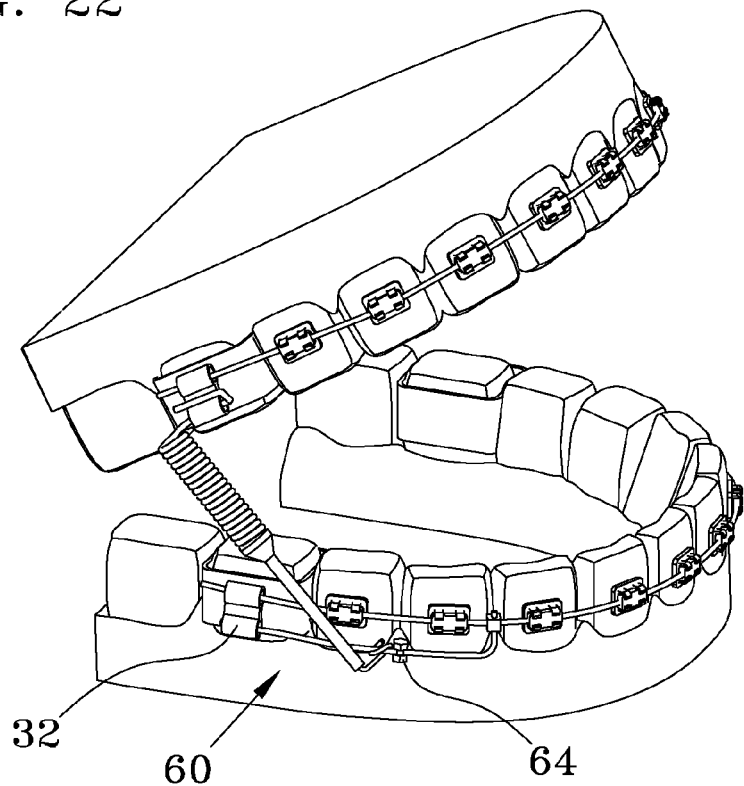
FIG. 23 is a left-side perspective view of a third alternate embodiment of the orthodontic appliance of the present invention installed on a dental model, with the dental model in an open position.
Figure 24:
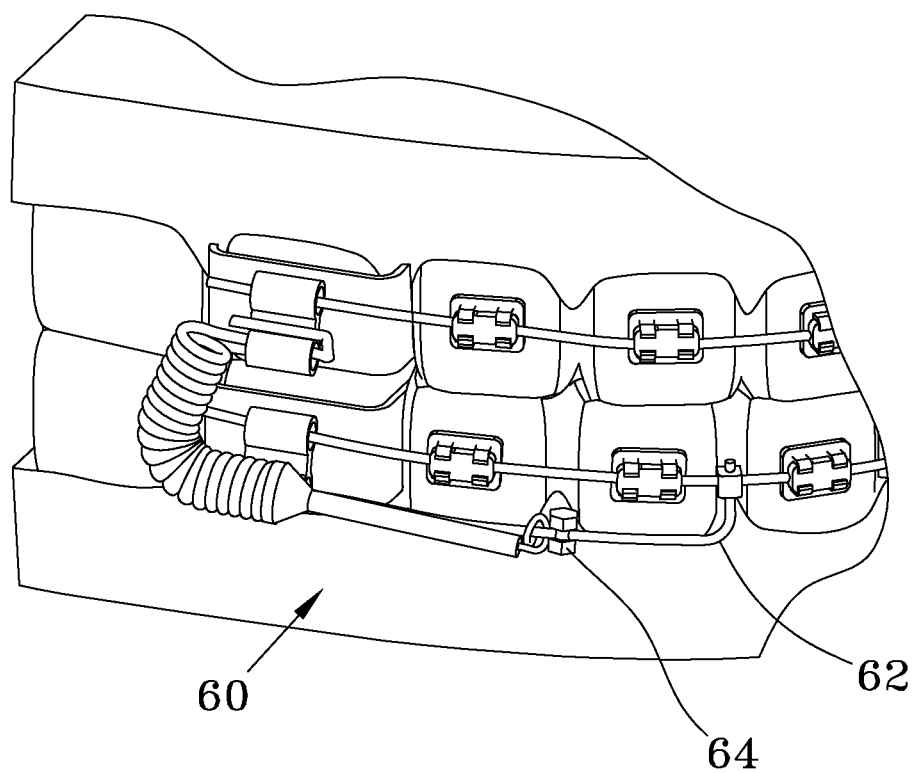
FIG. 24 is a partial left-side perspective view of a third alternate embodiment of the orthodontic appliance of the present invention installed on a dental model, with the dental model in a closed position.

FIGS. 22-24 illustrate third embodiment orthodontic appliance 60 installed on a dental model. FIGS. 22-24 illustrate orthodontic appliance 60 installed in an arrangement common in the art, wherein the appliance in coupled to a wire 62 that runs in a side-by-side, or generally parallel configuration to the archwire 24. Wire 62 is contained at a first end within a molar tube 32 and is connected at a second end to the archwire 24, as is well known in the art. Connecting third embodiment orthodontic appliance 60 (or second embodiment orthodontic appliance 50, or orthodontic appliance 10) to wire 62 allows the appliance 60 to be installed without removal of the bicuspid brackets, by the practitioner. To restrict the movement of the appliance 60 along wire 62 by an arch lock nut 64 (commonly available in the art).

Figure 30A:
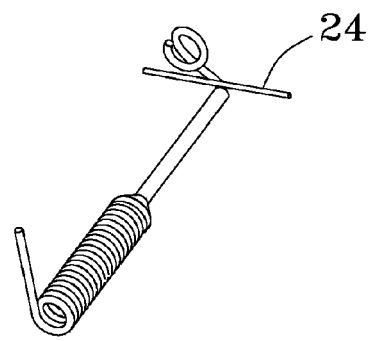
FIG. 30A illustrates the first step in installing the third alternate embodiment orthodontic appliance of the present invention on a section of archwire.
Figure 30B:
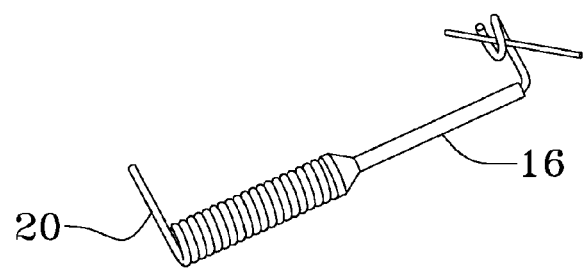
FIG. 30B illustrates the second step in installing the third alternate embodiment orthodontic appliance of the present invention on an section of archwire.
Figure 30C:
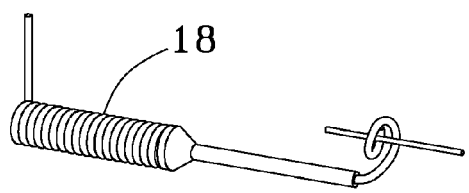
FIG. 30C illustrates the third alternate embodiment orthodontic appliance of the present invention installed on a section of archwire.

Third embodiment orthodontic appliance 60 is clearly illustrated in FIG. 25. Again, rigid member 16, force generating vector control module 18, and rear attachment wire 20, are all identical in construction and function as the previously discussed embodiments; however, pigtail attachment member 66 is a looped attachment, having a full 360° loop of wire, and is easily attached to an archwire as is illustrated in FIG. 30A-30C. Beginning with FIG. 30A, appliance 60 is positioned generally perpendicular to archwire 24, such that pigtail attachment 66 reside above archwire 24. Next, looking at FIG. 30B, appliance 60 is moved around archwire 24 (or wire 62), purposely trying to capture archwire 24 (or wire 62) within in it, finishing such that appliance 60 resides generally parallel to archwire 24 (or wire 62), when installed as illustrated in FIG. 30C. The installation process can simply be described as winding the pigtail attachment member around archwire 24 (or wire 62). Should appliance 60 break within in patient's mouth, the breakage will occur along the vector control module 18, and in a breakage scenario, pigtail attachment member 66 is advantageous because a patient can easily uninstall the pigtail attachment member 66 from the archwire 24 (or wire 62). The patient simply unwinds pigtail attachment member 66 from the archwire 24 (or wire 62), allowing the pigtail attachment member 66, rigid member 16, and a portion of broken vector control module 18 (the portion attached to rigid member 16) to be removed from his/her mouth.

Figure 29:
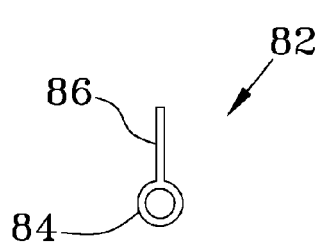
FIG. 29 is a front view of the pin-loop.

FIG. 26 and FIG. 27 illustrate possible variations to the rear attachment wire over previous embodiments. Looking at FIG. 26 fourth embodiment orthodontic appliance 70 is illustrated. Appliance 70 employs a pigtail attachment member 66, a rigid member 16, and a vector control module 18. However, while in previous embodiments rear attachment member 20 simply extended normally from the linear axis of the vector control module 18, looped rear attachment member 72, while still extending normally from vector control module 18, also comprised a looped portion 74. Looped rear attachment member 72 increases the life of the vector control module 18, creating an additional flex-point. Finally, illustrated in FIG. 27, fifth embodiment orthodontic appliance 80 completely omits either rear attachment member 20 or looped rear attachment member 72. Orthodontic appliance 80 instead employs an adjustable bracket 82 illustrated in FIG. 29 and shown on orthodontic appliance 80 in FIG. 28. Pin-loop 82 has two distinct portions, a circular portion 84, and a straight portion 86, extending normally from the circular portion 84. Circular portion 84 is designed to wind onto the terminal 88 of vector control module 18 and simply spin through the spring to reach a desired location as illustrated in FIG. 28. Once the practitioner has spun circular portion 84 though the loops of vector control module 18 to reach his/her desired location, straight portion 86 is inserted into molar tube/head gear tube 32, for secure attachment to the patient's upper jaw, and allowing for ease of removal should a breakage unfortunately occur. The patient simply unwinds the vector control module 18 out of pin-loop 82, leaving only pin-loop 82 in the patient's mouth until he/she can see can visit an orthodontist, since pigtail attachment member 66, rigid member 16 and the portion of the vector control module attached to rigid member 16 are easily removed via unwinding of pigtail attachment member 66 from archwire 24 (or wire 62) as previously discussed.

Although specific embodiments have been illustrated and described herein, it will be appreciated by those of ordinary skill in the art that a wide variety of alternate and/or equivalent implementations calculated to achieve the same purposes may be substituted for the specific embodiment shown and described without departing from the scope of the present invention. For example, it would simple and desirable to incorporate pin-loop 82 with twin-tab attachment member 52. Therefore, it is intended that this invention be limited only by the claims and the equivalents thereof.

The invention claimed is:

1. A orthodontic appliance for treating malocclusions, with a flexible end and a rigid end, wherein a flex point occurs at the mid-point of said flexible end, comprising:

a rigid member wherein said rigid member is elliptical or circular in cross-section;

a flexible coil spring containing said flex point;

an unwound extension of said coil spring for bendable attachment with a molar tube; and a looped attachment member for winding attachment with an archwire;

wherein said rigid member is secured to said flexible coil spring at a first end and said attachment member at a second end; and wherein said flex point occurs within 25-45% of a total appliance length from said unwound extension;

whereby said orthodontic appliance when installed in a patient's mouth exerts a gentle sweeping force, pushing on the patient's upper and lower jaws in an intrusive fashion.

2. The orthodontic appliance of claim 1 wherein said flexible coil is elliptical or circular in cross-section.

3. The orthodontic appliance of claim 1 wherein said looped attachment comprises at least a 360° loop of wire.

4. A orthodontic appliance for treating malocclusions, with a flexible end and a rigid end, wherein a flex point occurs at the mid-point of said flexible end, comprising:

a rigid member wherein said rigid member is rectangular in cross-section;

a flexible coil spring containing said flex point;

an unwound extension of said coil spring for bendable attachment with a molar tube; and a looped attachment member for winding attachment with an archwire, wherein said looped attachment member comprises at least a 360° loop of wire; and wherein said rigid member is secured to said flexible coil spring at a first end and said attachment member at a second end; and wherein said flex point occurs within 25-45% of a total appliance length from said unwound extension;

whereby said orthodontic appliance when installed in a patient's mouth exerts a gentle sweeping force, pushing on the patient's upper and lower jaws in an intrusive fashion.

5. A orthodontic appliance for treating malocclusions, with a flexible end and a rigid end, wherein a flex point occurs at the mid-point of said flexible end, comprising:

a rigid member wherein said rigid member is square in cross-section;

a flexible coil spring containing said flex point;

an unwound extension of said coil spring for bendable attachment with a molar tube; and a looped attachment member for winding attachment with an archwire, wherein said looped attachment member comprises at least a 360° loop of wire; and wherein said rigid member is secured to said flexible coil spring at a first end and said attachment member at a second end; and wherein said flex point occurs within 25-45% of a total appliance length from said unwound extension;

whereby said orthodontic appliance when installed in a patient's mouth exerts a gentle sweeping force, pushing on the patient's upper and lower jaws in an intrusive fashion.

* * * * *